United States Patent [19]

Hetz et al.

[11] Patent Number: 4,545,386
[45] Date of Patent: Oct. 8, 1985

[54] MANUALLY OPERATED ULTRASOUND APPLICATION

[75] Inventors: Walter Hetz, Erlangen; Peter Weber, Buckenhof, both of Fed. Rep. of Germany

[73] Assignee: Siemens AG, Berlin & Munich, Fed. Rep. of Germany

[21] Appl. No.: 487,784

[22] Filed: Apr. 22, 1983

[30] Foreign Application Priority Data

May 21, 1982 [DE] Fed. Rep. of Germany ....... 3219271

[51] Int. Cl.⁴ ............................................. A61B 10/00
[52] U.S. Cl. .................................................. 128/660
[58] Field of Search ............... 128/660, 661, 670, 361, 128/639, 640, 736, 738

[56] References Cited

U.S. PATENT DOCUMENTS

| | | | |
|---|---|---|---|
| 3,735,760 | 5/1973 | Vreeland, Jr. | 128/361 |
| 4,082,086 | 4/1978 | Page et al. | 128/640 |
| 4,250,894 | 2/1981 | Frei et al. | 128/774 |
| 4,305,401 | 12/1981 | Reissmueller | 128/690 |
| 4,327,738 | 5/1982 | Green et al. | |
| 4,363,326 | 12/1982 | Kopel | 128/24 A |
| 4,406,289 | 9/1983 | Wesseling et al. | 128/670 |

FOREIGN PATENT DOCUMENTS 6942159 10/1979 Fed. Rep. of Germany .
2950203  6/1980 Fed. Rep. of Germany .
0039045  4/1981 Fed. Rep. of Germany .

OTHER PUBLICATIONS

*Surgery-Into the Eye with Ultrasound,* Oct. 1964, Time Magazine, p. 96.
Roelandt et al., Ultrasonic Real Time Imaging with a Hand-Held-Scanner, Ultrasound in Med. & Biol., vol. 4, No. 2, pp. 93–97, 1978.
Mueller & Co., Obstetrical Instruments, 1956, p. 470, Membrane Perforators–Placenta Praevia Forceps.

Primary Examiner—Kyle L. Howell
Assistant Examiner—Ruth S. Smith
Attorney, Agent, or Firm—Mark H. Jay

[57] ABSTRACT

An ultrasound applicator designed for scanning tissues and organs located in cavities of the human body. A transducer head operated by an examining person is provided with a connection cable adapted to be connected to an image signal processing device. The transducer head is designed for firm placement of a guiding organ, especially the finger of an examining person. Preferably the top surface of the housing bears a recess forming a mold for the finger. Additionally, a flexible yoke may be arranged as a support element.

1 Claim, 6 Drawing Figures

MANUALLY OPERATED ULTRASOUND APPLICATION

BACKGROUND OF THE INVENTION

The invention relates to an ultrasound applicator for diagnosis; more specifically it relates to a manually operated ultrasound applicator suitable for examining internal organs and cavities of the human body, which applicator incorporates a transducer head, composed of a plurality of transducer elements built into an elongated, rigid housing having an scanning surface designed for placement onto the body area to be examined.

Ultrasound applicators of this type conventionally are designed for scanning internal organs of the human body from the outside through the skin, however it would be desirable to provide an ultrasound applicator designed for diagnosis of tissues or organs located in cavities of the human body which until now have been physically examined by hand. Physical examination has its limitations, it would be desirable to furnish a tool for medical examination providing precise readings and suitable for examining cavities in addition to or instead of physical examination.

The published German Patent Application No. 2,950,203, discloses an endoscope constituting an eye piece, a flexible tube, including bendable connecting portion and a cylinder-shaped front portion. A light conductor and control cables are arranged within the flexible tube and the front portion bears a built-in ultrasound transducer. The known endoscope is not very well adapted for use with examination of cavities because it cannot be sufficiently sterilized due to its sensitive optical system. In addition, the design of the bendable connecting portion renders the known endoscope applicable only for procedures requiring just relatively small bending angles. Therefore, possible applications of the known apparatus are rather limited.

European Patent Application No. 0,039,045 discloses another endoscope comprising a remotely controlled bendable front portion and two ultrasound transducers arranged therein. Similar to the mentioned endoscope, again the front portion of this endoscope has a relatively small bending angle, which most likely amounts to not more than a few degrees. The manipulation mechanism providing remote control and installed in the endoscope's interior is rather bulky, therefore the endoscope can only be applied to areas of sufficient dimensions.

A medical ultrasound testing probe is disclosed in the specification of German Utility Model No. 6,942,159, incorporating a handle at one end of a flexible tube and an ultrasound converter arranged at the other end. It is not possible to bend the ultrasound converter with respect to the adjacent end of the tube, which limits the use of the testing probe for examination of internal organs.

SUMMARY OF THE INVENTION

It is, therefore, a main object of the present invention to provide for an improved ultrasound applicator suitable for a variety of applications in examining cavities of the human body.

It is another object of the present invention to provide for a manually operated ultrasound applicator having small dimensions suitable for easy handling when utilized in such applications.

It is a further object of the present invention to provide for a simple, reliable testing tool which allows for examining of parts of the human body which until now are physically touched and examined by hand.

These objects, as well as other objects which will become apparent from the description which follows, are achieved by a manually operated ultrasound applicator for scanning of tissues and organs located in cavities of the body, the applicator including an ultrasound transducer, and a signal connection cord attached to said transducer head and adapted to be connected to an image signal processing device, and comprising means for guiding the transducer head like an integral appendage of an operator's finger.

The main advantage of this design in accordance with the present invention is that the transducer head can be adjusted in a simple manner by hand to suit any desired position in a wide range. This allows for any desired placement of the ultrasound applicator with respect to internal organs to be examined, at the back, front or side walls of such organ to be scanned. This tool is almost as capable of movement in any direction as a finger of the feeling hand of a surgeon with the extended scanning capability of a reliable scientific tool. The design renders it possible to make full use of the entire scanning surface, that is to say even examinations at large depths in cavities of the human body are made possible which were previously not possible due to small spatial expansions of the area to be examined or due to the depth of such areas which could not be reached by physical touching.

For a full understanding of the present invention, of further advantages and details, reference should now be made to the following description of preferred embodiments given in conjunction with the accompanying drawings.

DETAILED DESCRIPTION OF PREFERRED EMBODIMENTS

Figure 1:
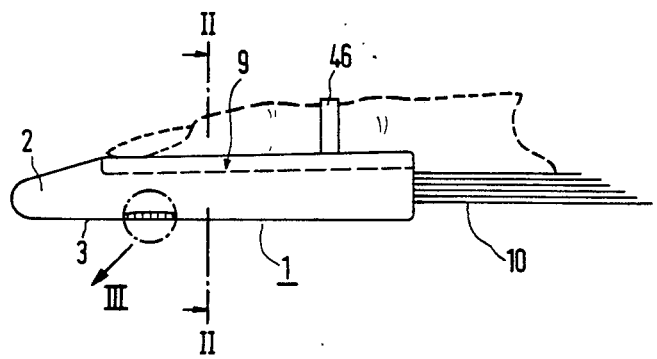
FIG. 1 shows schematically a side view of an ultrasound applicator designed according to the present invention for attachment to a finger.

FIG. 1 shows an ultrasound applicator or a transducer head 1 having an applicator housing 2. The housing 2 has a top surface and a bottom surface, the latter being a scanning surface 3.

Figure 3:
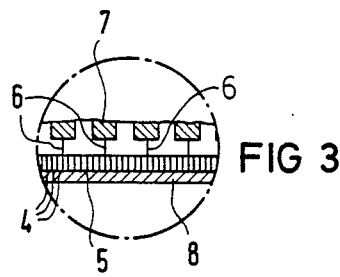
FIG. 3 shows a partial sectional view illustrating a detail of the applicator shown in FIG. 1 and referenced by III.

Details of this scanning surface are illustrated in the sectional view of FIG. 3 representing an enlarged section designated by reference III of FIG. 1. The ultrasound array is provided with a plurality of transducer elements 4 arranged adjacent to scanning surface 3.

These transducer elements 4 mounted in the housing 2 are finely segmented. A plurality (here, seven neighboring ones, but this is merely exemplary) of respective ones of these segmented transducer elements 4, are grouped together by a common electrical contact to form an element group 5. A total of 48 groups may be provided. Contact flags 6 of a contact comb each are used for contacting a respective group 5 and are embedded on a support member 7 also bearing the ultrasound transducer elements 4. The support member 7 may be composed of an epoxy resin having particles of oxidized tungsten powder implanted therein. A matching layer 8 for the transducer elements 4 forms the bottom surface, i.e. the scanning surface 3 of the housing 2, and may also be made of epoxy resin. The design concept of such an ultrasound transducer array comprising fine segmented transducer elements is known to those skilled in the art and is disclosed in more detail in U.S. Pat. No. 4,305,014; further detailed description is therefore deemed not to be necessary. Scanning surface 3 can vary in length depending upon the intended applications. In practice, the length of scanning surface 3 may be 3 cm.

A signal connection cord 10 is attached to the described sensor array. The arrangement of signal connection cord 10 enables a nearly tractionless trailing in any scanning direction selected for the ultrasound applicator. This is achieved by designing this multi-wire cable of a multi-strip line bent to form a sickle shaped cross-section, which allows for placement of a finger and can easily be held in the palm of the hand of the examining person. The connection cord 10 provides a means to connect the ultrasound applicator to any conventional image processing and display device (not shown). A more detailed description of such device is not deemed to be necessary, since it forms no part of the present invention and a variety of devices which may be utilized for displaying scanning results is known to those skilled in the art.

Figure 2:
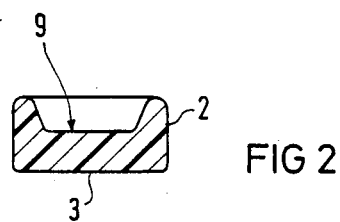
FIG. 2 shows a sectional view of the applicator shown in FIG. 1 taken along line II—II.

FIGS. 1 and 2 illustrate, furthermore, a recess 9 arranged in the top surface of the housing 2. FIG. 1 depicts schematically how the ultrasound applicator can be applied to a finger, shown in broken lines. FIG. 2 is a cross-sectional view of the transducer 1 taken along line II . . . II. This sectional view represents in particular the concave depression provided for that purpose and forming a finger mold. In this manner the design of the housing 2 is well suited for a firm placement of a finger of the examining person which allows for reliable scanning examinations to be performed with the ultrasound applicator 1 when applied to the finger.

In order to position the ultrasound applicator 1 at the finger of an examining person, additionally a yoke 46 is provided which may be composed of just an elastic strip. As an alternative, a finger cot made of material pervious to ultrasound-waves, i.e. latex, may be utilized, which cot is slipped over the transducer 1 positioned on the finger.

Figure 4:
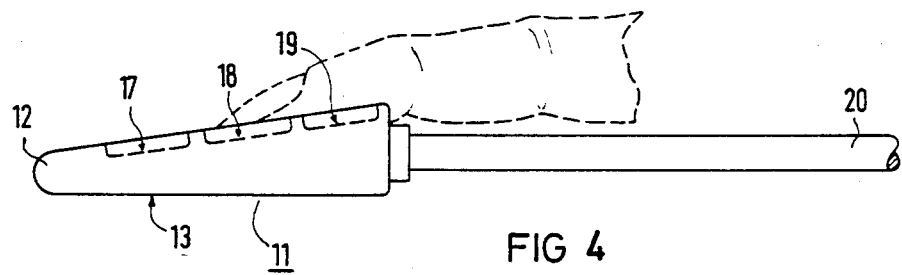
FIG. 4 shows a side view of another embodiment of the ultrasound applicator incorporating several finger molds for a firm grip.

FIG. 4 represents another embodiment of an ultrasound applicator constituting a transducer 11 including a housing 12 and a scanning surface 13. In the top surface there are arranged three finger molds 17, 18, 19 which are individually cut into the top surface to support the guiding finger of the examining person at various distances. In this case, connection cord 20 attached to transducer member 11 with conventional traction support is provided in the form of a round cable.

Figure 5:
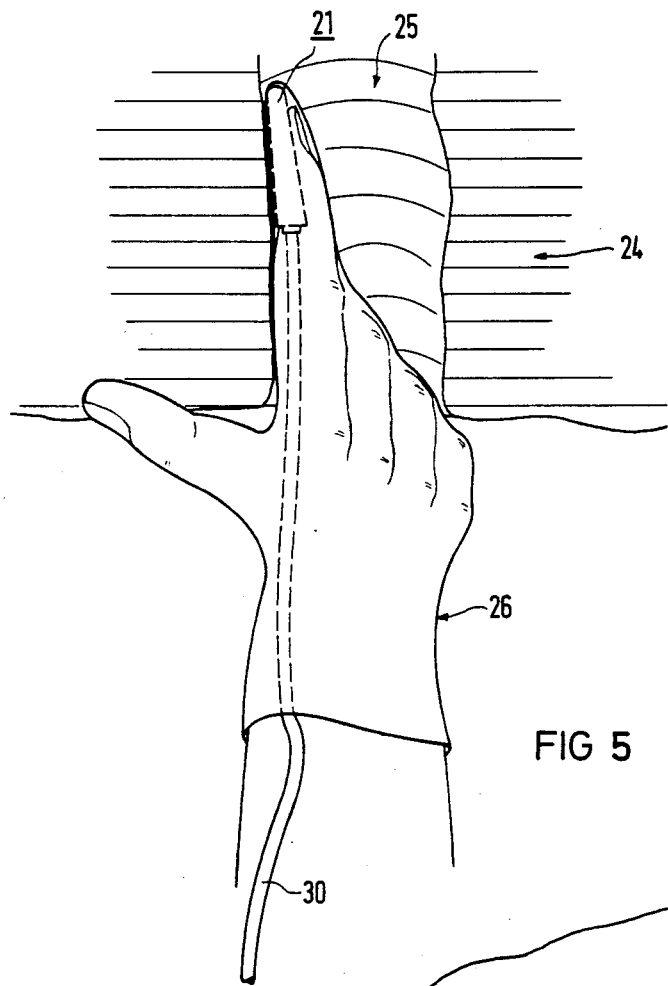
FIG. 5 represents a schematic illustrating a possible application of an ultrasound applicator according to the present invention for examining of internal cavities of the human body.

The ultrasound applicators described above in conjunction with FIGS. 1 through 4 are especially designed for use with urological and gynecological examination previously performed only by manual examination. During these procedures, the tissues forming the passage wall of the rectum, the urethra and vagina, respectively are conventionally touched and felt with the index finger. An application of the arrangement in accordance with the present invention is schematically illustrated in FIG. 5. The body region identified by numeral 24 includes a passage way 25. The hand of the examining person wears a flexible glove 26 made of material pervious to ultrasound waves which material can be latex or any similar material. The ultrasound applicator 21 and a portion of its connection cable 30 are also covered by the glove 26. Thereby, a scanning procedure is performed, which will result in much more precise diagnosis due to the generated ultrasound image of the region under examination.

Figure 6:
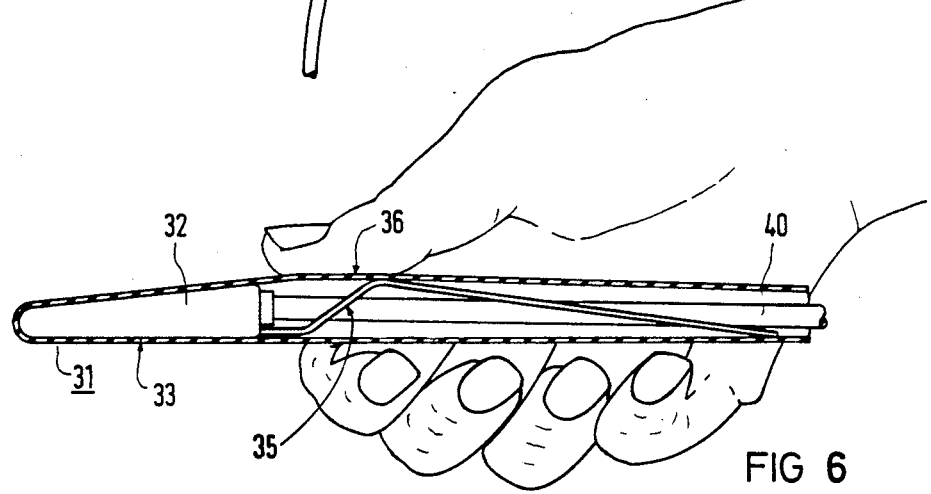
FIG. 6 shows another embodiment of the present invention, i.e. an applicator having a grip member removably attached thereto.

The embodiment shown in FIG. 4 comprises several finger molds for reaching various depths. Nevertheless, there are applications when an area to be examined can no longer be reached by a finger. To this reason, an extension grip can be provided as manipulative support device, as represented by FIG. 6. A spring like bent metal strip 35 is removably attached to housing 32 of the transducer 31. The entire ultrasound applicator including transducer 31, metal strip 35, and connection cable 40 are enveloped by a flexible cover 36 which is pervious to ultrasound waves and may be made of latex. Thereby, a penlike handle for ultrasound applicator 31 is formed, wherein the cover warrants the sterility of the entire instrument. Metal strip 35 can be of any predetermined geometrical design, i.e. it can be offset to provide certain attachment positions. An end of metal strip 35 can be inserted into or clamped to applicator housing 32 to facilitate easy replacement. In summary, the instrument described above enables even scanning of previously inaccesible body regions. As a result, diagnosis may be had of areas which were previously not accessible for a careful investigation by physical examination due to the depth of the location of the internal organ or tissue under examination.

There have thus been shown and described different embodiments of a novel hand held ultrasound applicator which fulfills all the objects and advantages sought therefor. Many changes, modifications, variations and other uses and applications of the subject invention will, however, become apparent to those skilled in the art after considering the specification and the accompanying drawings, which disclose preferred embodiments thereof. The described application with respect to an examination of a cavity of the human body does not limit the variety of possible applications, but presents only an appropriate example for investigating internal organs or other parts of the human body to be examined by means of such an ultrasound applicator. All changes, modifications, variations and other uses and applications which do not depart from the spirit and scope of the invention are deemed to be covered by the invention which is limited only by the claim which follow.

What is claimed is:

1. A manually operated ultrasound applicator for use in body cavities, said ultrasound applicator comprising:
   (a) an ultrasound array containing a plurality of ultrasound transducer elements;
   (b) an elongated housing containing said ultrasound array, said housing having a scanning surface for placement on an area under examination and a concave and elongated top surface opposed to said scanning surface and shaped to accommodate a bottom surface of a user's fingertip;

(c) a connection cable electrically connected to said ultrasound array and adapted for coupling to an image signal processing device; and (d) a yoke mounted on the housing and located above its top surface and being shaped to receive a user's fingertip, thereby detachably securing the housing to a distal end of a user's fingertip.

* * * * *